United States Patent [19]

Suverkropp

[11] 3,932,491
[45] Jan. 13, 1976

[54] PROCESS FOR OPTICAL RESOLUTION OF RACEMIC LYSINE SULPHANILATE

[75] Inventor: Geertrudes H. Suverkropp, Geleen, Netherlands

[73] Assignee: Stamicarbon B.V., Geleen, Netherlands

[22] Filed: Apr. 8, 1974

[21] Appl. No.: 459,237

[30] Foreign Application Priority Data
May 7, 1973   Netherlands.................... 7306318

[52] U.S. Cl. .......................................... 260/501.12
[51] Int. Cl.² ...................................... C07C 143/58
[58] Field of Search ............................. 260/501.12

[56] References Cited
UNITED STATES PATENTS

| | | | |
|---|---|---|---|
| 2,934,561 | 4/1960 | Rogers | 260/501.12 |
| 3,527,776 | 9/1970 | Uzuki et al. | 260/501.12 |
| 3,742,041 | 6/1973 | Chibata et al. | 260/501.12 |

FOREIGN PATENTS OR APPLICATIONS

| | | | |
|---|---|---|---|
| 1,250,557 | 10/1971 | United Kingdom | 260/501.12 |
| 1,191,100 | 5/1970 | United Kingdom | 260/501.12 |

Primary Examiner—James O. Thomas, Jr.
Assistant Examiner—Nicky Chan
Attorney, Agent, or Firm—Cushman, Darby & Cushman

[57] ABSTRACT

Optical resolution of lysine in the form of racemic lysine sulphanilate is enhanced by the addition to the supersaturated solution of racemic lysine sulphanilate of one or more substances which suppress the formation of seeds of racemic lysine sulphanilate in the supersaturated solution. Among the seed-suppressing substances which may be added are lysine, lysine acetate, lysine carbonate, amino acetic acid and glycerol. The yield of optically active lysine sulphanilate is improved according to the disclosed process.

3 Claims, No Drawings

PROCESS FOR OPTICAL RESOLUTION OF RACEMIC LYSINE SULPHANILATE

BACKGROUND OF THE INVENTION

The present invention relates to a process for optical resolution of racemic lysine sulphanilate. It is known, for example in British patent specifications Nos. 1,191,100 and 1,250,557, that racemic lysine sulphanilate can be resolved optically by subjecting a supersaturated solution of racemic lysine sulphanilate to selective crystallization and by separating the optically active lysine sulphanilate, which has then crystallized out, from the mother liquor. From the L-lysine sulphanilate so obtained, L-lysine, as such or in the form of a customary L-lysine compound, can be recovered, which is useful as an additive for human and animal food.

The use of sulphanilic acid as an auxiliary acid for optical resolution of racemic lysine has an advantage, in comparison with the use of another optically active auxiliary acid, in that it does not itself become racemized during the various processing steps. A disadvantage to the use of sulphanilic acid for optical resolution of racemic lysine, however, is that the yield of optically active lysine sulphanilate in the selective crystallization is rather small, so that a much larger recirculation is necessary than would be the case with the use of an optically active acid, for instance optically active alpha-phenoxypropionic acid, in which the required diastereoisomer-salt can be separated off with a very satisfactory yield through fractional crystallization.

DETAILED DESCRIPTION OF THE INVENTION

It has now been found that there are specific substances which, when dissolved in the supersaturated solution of racemic lysine sulphanilate, can hinder or suppress the spontaneous formation of seeds of racemic lysine sulphanilate in the supersaturated solution, so that a greater supersaturation is obtained and, hence, a substantially higher yield of selectively crystallized optically active lysine sulphanilate with a high optical purity can be obtained. Examples of said substances are lysine, lysine acetate, lysine carbonate, amino acetic acid and glycerol.

The present invention, therefore, provides a process for optical resolution of racemic lysine sulphanilate by subjecting a supersaturated solution containing racemic lysine sulphanilate to selective crystallization and by separating the lysine sulphanilate, which has crystallized out, from the mother liquor, the process being characterized in that, in the selective crystallization, the beginning supersaturated solution contains a substance dissolved therein which hinders the spontaneous formation of seeds of racemic lysine sulphanilate.

For interference with the seed formation, preferably lysine, lysine acetate or lysine carbonate are applied since these substances are particularly suited, chemically, for use with the racemic lysine sulphanilate to be resolved. Lysine is highly suitable and, hence, is preferred. With the aid of this compound, the yield can be increased to a sufficient degree, while at the same time, it is also the compound which, actually, is to be resolved optically via the resolution of racemic lysine sulphanilate. While it is possible to use mixtures of two or more of these seed-suppressing materials, it is usually preferable to employ only one material at a time.

The quantity of substance added to the supersaturated solution and used for interference with seed formation may be varied, for instance between about 0.01 and about 2 g per g of dissolved lysine sulphanilate contained in the supersaturated starting solution. For practical purposes an amount of about 0.05 to about 1.5 g per g of dissolved lysine sulphanilate in the supersaturated starting solution appears to be highly suitable.

As used herein the term lysine sulphanilate has the same meaning as lysine para-aminobenzene sulfonate.

The supersaturated starting solution may be obtained according to known procedures, for instance by cooling a solution or by concentrating it by evaporation, in which solution the racemic lysine sulphanilate and the substance which hinders seed formation (identified above) have been dissolved. As for the solvent, while water is very satisfactory, other solvents may also be used, such as mixtures of water and the lower alkanols, i.e., methanol, ethanol, propanol, as well as water plus acetone or butanone.

The technique of optical resolution of racemic lysine sulphanilate by selective crystallization of a supersaturated solution thereof is already well known in the art and is described in British Pat. Nos. 1,191,100 and 1,250,557, the disclosures of which are hereby incorporated by reference to the extent necessary to better appreciate the present invention.

The selective crystallization may be brought about by seeding into the supersaturated solution crystals of the optically active lysine sulphanilate to be crystallized out, or by passing the supersaturated solution over a fixed bed of the optically active lysine sulphanilate to be crystallized out. In case the two antipodes of lysine sulphanilate are present in the supersaturated solution in unequal quantities, the antipode present in a larger quantity may also crystallize selectively through spontaneous crystallization. However, in that case the selective crystallization is, preferably, also brought about by contacting the supersaturated solution with crystals of the antipode to be crystallized out. The particle size of the crystals added to the supersaturated solution may be varied. A particle size of less than 0.05 mm can be used with a good result, though a particle size above 0.05 mm, e.g. between 0.05 and 0.2 mm, is also suitable.

In practice, the process according to the present invention may be realized using methods known in the field of selective crystallization optical resolution, in which various conditions, such as the degree of supersaturation, the crystallization time, the crystallization temperature, the size and the quantity of the seed crystals, may be varied. For instance, the supersaturated solution may be separated into two equal parts, and a quantity of L-antipode crystallized selectively out of the one part and an equal quantity of D-antipode crystallized selectively out of the other part, and return the two remaining mother liquors, after mixture, to the section for preparation of the supersaturated starting solution. It is also possible for a quantity of the one antipode to be crystallized selectively out of the supersaturated solution, for a quantity of the other antipode to be crystallized selectively out of the remaining mother liquor, and for the mother liquor then left behind to be used in the preparation of the supersaturated starting solution. An example of yet another method for such procedures is the one in which the mother liquor remaining after a quantity of the one antipode has crystallized out selectively is processed by causing the mother liquor to become saturated, or virtually saturated, with racemic lysine sulphanilate, a quantity of the other antipode then being obtained in the solid state.

The L-lysine sulphanilate obtained according to the present invention may be separated into its components in various ways, for instance by passing an aqueous solution of the salt over a weakly basic ion exchanger. The sulphanilic acid is then bound on the ion exchanger, while a lysine solution is obtained as eluate. Also, an aqueous solution of the optically active lysine sulphanilate may be passed over a strongly acid ion exchanger in the $NH_4^+$ form. The lysine is then bound to the ion exchanger and may be washed out by means of dilute ammonia water. Ion exchange resins suitable for use in the above procedures are disclosed in Vol. 7, *Encyclopedia of Polymer Science and Technology*.

The present invention will be further explained by way of the following illustrative examples, all parts and percentages being expressed by weight unless otherwise indicated.

EXAMPLE 1

Racemic lysine sulphanilate (30 g) was dissolved, with sufficient heating, in an aqueous solution (45 g) containing DL-lysine (21.8% by weight), whereupon the clear solution was supersaturated by cooling to 25°C. To the supersaturated solution solid L-lysine sulphanilate (2.5 g, crystal size smaller than 0.05 mm) was added, following which the suspension obtained was stirred at 25°C for 15 minutes. Next, the L-lysine sulphanilate which crystallized out was separated by filtration from the mother liquor, washed on the filter with methanol (approximately 20 ml), and dried. 8.7 g of L-lysine sulphanilate were obtained.

In order to determine the optical purity of the L-lysine sulphanilate so obtained, the salt was converted into L-lysine monohydrochloride. To this end, the 8.7 g of L-lysine sulphanilate obtained were dissolved in water (35 ml) and the resulting solution was passed over a column filled with about 150 ml of a strongly acid ion exchanger (Dowex 50) in the $NH_4^+$ form. The column was reflushed with demineralized water until ammonium sulphanilate was no longer present in the eluate. The lysine bound to the ion exchanger was washed out with 3.5 N ammonia water, whereupon the eluate obtained was concentrated by evaporation at a reduced pressure in order to remove the ammonia. The lysine solution so obtained was neutralized with the required quantity of hydrochloric acid (1 mole per mole of lysine) and was then evaporated until fully dry. L-lysine monohydrochloride (5 g) with a specific rotation of : $|\alpha|_D^{20} = 27.2$ (lysine concentration = 10; 6 N HCL) were obtained. From this follows an optical purity for the L-lysine sulphanilate obtained of 100%. The resolution efficiency (defined as $$\frac{a \times \frac{b}{100} - c}{d} \times 100\%,$$

in which $a$, $c$ and $d$ respectively represent the quantity of L-lysine sulphanilate obtained, the quantity of seed material and the quantity of L-lysine sulphanilate in the starting material, expressed in grams, and $b$ the optical purity, expressed in percents) amounts to 41.4%.

EXAMPLE 2

Racemic lysine sulphanilate (41 g) is dissolved, by heating in aqueous DL-lysine solution (50 g, 10% by weight of DL-lysine), whereupon the resulting clear solution was supersaturated by being cooled to 25°C. Subsequently, solid L-lysine sulphanilate (5 g, crystal size smaller than 0.05 mm) was added, and the suspension obtained was stirred at 25°C for 5 minutes. The L-lysine sulphanilate which had crystallized out was then filtered off and washed on the filter with methanol (about 20 ml). L-lysine sulphanilate (12.84 g) with an optical purity of 89.6% (89.6% by weight of the L-antipode in addition to 10.4% by weight of DL) is obtained. The resolution efficiency amounts to 32%.

COMPARATIVE EXAMPLE

Racemic lysine sulphanilate (50 g) was dissolved, by being heated, in water (50 g), whereupon the resulting solution was supersaturated by cooling to 25°C. In this solution, as was the case in the Examples 1 and 2, the racemic lysine sulphanilate concentration was 10% by weight higher than the racemic lysine sulphanilate concentration in a saturated aqueous solution at 25°C, which amounted to 40% by weight. Subsequently, solid L-lysine sulphanilate (4.2 g, crystal size smaller than 0.05 mm) was added and the suspension obtained was stirred at 25°C for 5 minutes. The L-lysine sulphanilate which had crystallized out was then filtered off and washed on the filter with methanol (approximately 20 ml). L-lysine sulphanilate (16.5 g) having an optical purity of 43.8% was obtained. The resolution efficiency amounted to 12%.

EXAMPLE 3

Racemic lysine sulphanilate (7.8 g) was dissolved, by being heated, in a mixture of 45 g of water and 5 g of racemic lysine acetate, whereupon the clear solution was cooled to 25°C. Subsequently, solid L-lysine sulphanilate (2.5 g, crystal size smaller than 0.05 mm) was added and the suspension obtained stirred for 10 minutes at 25°C. The L-lysine sulphanilate which had crystallized out was filtered off and washed on the filter with methanol (about 20 ml). L-lysine sulphanilate (11.82 g), having an optical purity of 85% was obtained. The resolution efficiency amounted to 39.2%.

EXAMPLE 4

Racemic lysine sulphanilate (35 g) was dissolved, with sufficient heating, in a mixture of water (36.1 g) and glycerol (1.9 g), whereupon the clear solution was supersaturated by cooling to 25°C. Subsequently, solid L-lysine sulphanilate (2 g, crystal size smaller than 0.05 mm) was added and the resulting suspension was stirred for 15 minutes at 25°C. The L-lysine sulphanilate which had crystallized out was then filtered off and washed on the filter with methanol (about 20 ml). L-lysine sulphanilate (9.28 g) having an optical purity of 85% was obtained. The resolution efficiency amounted to 33.7%.

EXAMPLE 5

Racemic lysine sulphanilate (35 g) was dissolved, by being heated, in a mixture of water (39.15 g) and amino acetic acid (4.35 g), whereupon the clear solution was supersaturated by being cooled to 25°C. Next, solid L-lysine sulphanilate (2 g, crystal size smaller than 0.05 mm) was added and the resulting suspension was stirred for 10 minutes at 25°C. The L-lysine sulphanilate which had crystallized out was then filtered off and washed on the filter with methanol (about 20 ml). Optically pure L-lysine sulphanilate (7.88 g) was obtained. The resolution efficiency amounted to 33.6%.

EXAMPLE 6

Racemic lysine sulphanilate (44 g) was dissolved by being heated, in an aqueous DL-lysine carbonate solution (56 g, 10% by weight of DL-lysine carbonate), whereupon the resulting clear solution was supersaturated by being cooled to 25°C. Next, solid L-lysine sulphanilate (5.0 g, crystal size smaller than 0.05 mm) was added and the resulting suspension was stirred for 5 minutes at 25°C. The L-lysine sulphanilate which had crystallized out was then filtered off and washed on the filter with methanol (about 20 ml). L-lysine sulphanilate (13.1 g) having an optical purity of 92.6% was obtained. The resolution efficiency amounted to 32.4%.

What is claimed is:

1. In a process for resolving DL-lysine sulphanilate comprising the steps of preparing a supersaturated solution of DL-lysine sulphanilate in water, seeding the supersaturated solution with crystals of the desired enantiomer of the DL-lysine sulphanilate to cause crystallization of the desired enantiomer to take place, and recovering the separated crystals, the improvement comprising during the preparation of the supersaturated solution and prior to seeding adding a compound selected from the group consisting of DL-lysine, DL-lysine acetate, DL-lysine carbonate, amino acetic acid and glycerol, present in an amount of from about 0.01 to about 2 g. per gram of dissolved lysine sulphanilate contained in the supersaturated starting solution, which compound suppresses crystallization of racemic lysine sulphanilate during the crystallization of the desired enantiomer.

2. The process of claim 1 wherein the supersaturated solution contains from about 0.05 to about 1.5 grams of added compound per gram of dissolved DL-lysine sulphanilate.

3. The process of claim 1 wherein DL-lysine is the compound added to the supersaturated solution.

\* \* \* \* \*